United States Patent
Frese et al.

(10) Patent No.: US 8,811,654 B2
(45) Date of Patent: Aug. 19, 2014

(54) NON-DESTRUCTIVE DETERMINATION OF MATERIAL CHARACTERISTICS

(75) Inventors: Tanja Frese, Horstedt (DE); Klaus Edelmann, Bremen (DE)

(73) Assignees: Airbus Operations GmbH, Hamburg (DE); Premium Aerotec GmbH, Augsburg (DE)

( * ) Notice: Subject to any disclaimer, the term of this patent is extended or adjusted under 35 U.S.C. 154(b) by 140 days.

(21) Appl. No.: 13/524,354

(22) Filed: Jun. 15, 2012

(65) Prior Publication Data

US 2012/0321126 A1  Dec. 20, 2012

Related U.S. Application Data

(60) Provisional application No. 61/497,863, filed on Jun. 16, 2011.

(30) Foreign Application Priority Data

Jun. 16, 2011 (DE) .......................... 10 2011 104 435

(51) Int. Cl.
*G06K 9/00* (2006.01)

(52) U.S. Cl.
USPC ........................................................ 382/100

(58) Field of Classification Search
None
See application file for complete search history.

(56) References Cited

U.S. PATENT DOCUMENTS

| | | | |
|---|---|---|---|
| 5,332,178 A * | 7/1994 | Williams | 244/123.3 |
| 5,341,436 A | 8/1994 | Scott | |
| 5,963,660 A | 10/1999 | Koontz et al. | |
| 6,632,015 B2 | 10/2003 | Nagasawa | |
| 7,197,177 B2 | 3/2007 | Lowe | |
| 7,239,340 B2 | 7/2007 | Breuer et al. | |
| 7,867,562 B2 | 1/2011 | Wisniewski et al. | |
| 8,208,148 B2 | 6/2012 | Lengsfeld et al. | |
| 8,467,069 B2 | 6/2013 | Edelmann et al. | |
| 2008/0232555 A1* | 9/2008 | Hoernig | 378/207 |
| 2010/0189325 A1* | 7/2010 | Garg | 382/131 |

FOREIGN PATENT DOCUMENTS

| | | |
|---|---|---|
| DE | 19650876 A1 | 6/1998 |
| DE | 202007012346 U1 | 12/2007 |
| DE | 112008001385 T5 | 4/2010 |

OTHER PUBLICATIONS

German Patent Office, German Office Action date Feb. 23, 2012 for German Patent Application No. 10 2011 104 435.7.
European Patent Office, Extended European Search Report dated Apr. 23, 2013 for European Patent Application No. 12170929.9.

\* cited by examiner

*Primary Examiner* — Nirav G Patel
(74) *Attorney, Agent, or Firm* — Ingrassia Fisher & Lorenz P.C.

(57) ABSTRACT

A non-destructive determination of material characteristics of an aircraft component is provided. To provide a simple determination of material characteristics, which can be implemented economically, it is provided to make available image data of a layer, which can be detected from outside using electromagnetic radiation, of a workpiece to be examined; to detect first areas having a first pixel characteristic using the image data; and to detect second areas having a second pixel characteristic using the image data; the first pixel characteristic being associated with a fiber inlay of a fiber composite layer; and the second pixel characteristic being associated with an at least part-crystalline thermoplastic polymer of the fiber composite layer, which thermoplastic polymer is in a crystalline state; and to determine a relationship of the first areas to the second areas.

18 Claims, 15 Drawing Sheets

NON-DESTRUCTIVE DETERMINATION OF MATERIAL CHARACTERISTICS

CROSS-REFERENCE TO RELATED APPLICATIONS

This application claims priority to German Patent Application No. 10 2011 104 435.7, filed Jun. 16, 2011, and to U.S. Provisional Patent Application No. 61/497,863, filed Jun. 16, 2011, which are each incorporated herein by reference in its entirety.

TECHNICAL FIELD

The technical field relates to non-destructive determination of material characteristics of an aircraft component. The present disclosure relates more particularly to a determination device for the non-destructive determination of material characteristics of an aircraft component, to a system for non-destructive determination of material characteristics of an aircraft component, to a method for non-destructive determination of material characteristics of an aircraft component and to a computer program element and a computer-readable medium.

BACKGROUND

In the production of aircraft components, material characteristics are determined for test and quality control purposes. For example, in case of thermoplastic fabric-reinforced components or parts, a quality control by means of differential scanning calorimetry (DSC) is used. However, this is very time-intensive and is associated with high costs and means that material is actually removed, which is associated with a logistical expense, i.e. possible destruction of the component or at least a change in the component when the component has already been finished.

In addition, other objects, desirable features and characteristics will become apparent from the subsequent summary and detailed description, and the appended claims, taken in conjunction with the accompanying drawings and this background.

SUMMARY

Therefore, there is a need to provide a method for determining material characteristics, which can be carried out in a simpler and more cost-effective manner.

It is pointed out that the various aspects of the disclosure described below apply to the ascertainment device for non-destructive determination of material characteristics of an aircraft component, to the system for non-destructive determination of material characteristics of an aircraft component, to the method for non-destructive determination of material characteristics of an aircraft component as well as to the computer program element and the computer-readable medium. It is also pointed out that the various embodiments described below relate equally to the devices, the method, the computer program element and the computer-readable medium.

Of course, the individual features can also be combined with one another, as a result of which some advantageous effects can also be produced which go beyond the sum of the individual effects.

According to various aspects, an ascertainment device for non-destructive determination of material characteristics of an aircraft component is provided which comprises a data transmission means and an arithmetic-logic unit. The data transmission means is configured to provide image data of a layer, which can be optically detected from outside, of a workpiece to be examined. The arithmetic-logic unit is configured to detect first areas having a first pixel characteristic and second areas having a second pixel characteristic using the image data, the first pixel characteristic being associated with a fiber inlay of a fiber composite layer and the second pixel characteristic being associated with an at least part-crystalline thermoplastic polymer of the fiber composite layer, which thermoplastic polymer is in a crystalline state. The arithmetic-logic unit is also configured to determine the relationship of the first areas to the second areas.

According to various aspects, a system for non-destructive determination of material characteristics of an aircraft component is provided, which comprises a recording device for the generation of image data, as well as an ascertainment device according to the above-mentioned aspect. The recording device is configured to record image data of a layer, which can be optically detected from outside, of a workpiece to be examined. The recording device transmits the image data to the arithmetic-logic unit via the data transmission means.

According to various apsects, a method for non-destructive determination of material characteristics of an aircraft component is provided which comprises the following: a) providing of image data of a layer, detectable from outside using electromagnetic radiation, of a workpiece to be examined; b) detecting first areas having a first pixel characteristic using the image data, and detecting second areas having a second pixel characteristic using the image data, the first pixel characteristic being associated with a fiber inlay of a fiber composite layer and the second pixel characteristic being associated with an at least part-crystalline thermoplastic polymer of the fiber composite layer, which thermoplastic polymer is in a crystalline state; and c) determining of the relationship of the first areas to the second areas.

The term "pixel characteristic" denotes the parameters of brightness and/or color of a pixel, i.e. the pixel parameters. In this respect, the pixel characteristic can relate to parameter ranges, for example a range comprising a plurality of values, or also to a single value.

The term "brightness" relates to a range of brightness values, for example a range of grey values or also a single grey/brightness value. The term "color" relates to a range of color values, or also to a single color value.

The detectable layer of the workpiece to be examined can form the outer layer of the workpiece. The detectable layer can also be at least partly covered by a layer, which is at least partly transparent to electromagnetic radiation.

Thermoplastic material can be provided inside the workpiece. For example, the interior of the workpiece can have a fiber composite construction in which fibers are embedded in a matrix, for example in a plastics material matrix. Additional layers or materials, known as mixed structures, for example glass fiber-reinforced inlays can also be provided inside the workpiece.

The image data can comprise a unit cell, based on an image detail, which unit cell has a fixed number of recurring image patterns or image structures.

According to various exemplary embodiments, a pixel characteristic course for the image data is determined for the determination of the relationship.

Thresholds for the first pixel characteristic and/or for the second pixel characteristic can be predetermined for the detection of the first and second areas.

A color gradient and/or a histogram, for example, is/are produced as the pixel characteristic course. A histogram or a brightness value distribution curve for the image data can be determined for the determination of the relationship.

A grey value distribution curve for the image data and/or a color distribution curve can be determined for the determination of the relationship.

As an alternative or in addition, the first areas having the first pixel characteristic and the second areas having the second pixel characteristic can also be detected and compared with one another, for example by determining the totalled surface area measurements in each case.

According to various exemplary embodiments, the relationship of the first areas to the second areas can be provided, for example indicated, or output as a print.

According to various exemplary embodiments, the relationship of the first areas to the second areas can be associated with reference information.

For example, a target curve or a target histogram can be displayed.

According to various exemplary embodiments, for a) the image data of the workpiece to be examined are recorded using electromagnetic radiation.

For example, the image data are generated by means of light, the optical differentiation into first areas and second areas being carried out in visible light or invisible light.

The workpiece to be examined can be guided along a recording device, for example a scanner or a camera, and the image data are provided by the recording device. For example, a video camera can be provided to capture a sequence of images, a selection being provided in order to select from the sequence one photograph as image data. The image data can be recorded or provided from different sides of the workpiece, and a) to c) can be carried out in parallel for the different sides.

According to various exemplary embodiments, in a), reference image data having first and second reference pixel characteristics are provided which have been generated together with the image data, a reference relationship being stored and the relationship of the first areas to the second areas being assessed using the reference relationship.

For example, a reference item is detected together with the workpiece to thus form a criterion for the pixel characteristic (s), for example the brightness or the brightness values or colors or color values. For example, a pattern with first pattern areas, which have an established first pixel characteristic and having second pattern areas, which have an established second pixel characteristic can be provided, for example a chessboard pattern.

According to various exemplary embodiments, the thermoplastic polymer can have a crystalline form or an amorphous form, it being possible to visually distinguish the crystalline form from the amorphous form, and it being possible to visually distinguish the fiber inlay from the crystalline form of the thermoplastic polymer.

According to various exemplary embodiments, d) is provided in which the relationship from c) is associated with an established degree of crystallinity of the workpiece.

The degree of crystallinity can be output, for example indicated to the user, for example, by the arithmetic-logic unit or can be used for further computational sequences.

The relationship from c) can be associated with an established material characteristic.

The detection of the outer layer or of the layer visible from outside in the case of a cover is adequate, because, based on the thickness, slower cooling generally takes place in the center of the workpiece, and thus a greater or better crystallinity can form. Consequently, the value on the outside is always lower.

The fiber inlay can comprise heavy-duty fibers for the transmission of force.

According to various exemplary embodiments, the first pixel characteristic is associated with a fiber inlay which comprises carbon fibers.

The fiber inlay can include of carbon fibers. The fiber inlay can also include aramid fibers. Furthermore, the fiber inlay can include glass fibers which have been produced from colored glass, for example, or have been dyed. The fiber inlay can also include metal fibers or ceramic fibers. The fibers can also be used in a mixed form.

The fiber inlay can be a bidirectional or multidirectional woven fabric or non-woven fabric. As an alternative or in addition, the fiber inlay can also have a plurality of unidirectional fibers. Furthermore, in addition or alternatively, the fiber inlay can have a plurality of undirected fibers, i.e. it can have a fleece structure of the fibers.

The thermoplastic polymer includes, for example, polyphenylene sulphide (PPS). The thermoplastic polymer can also include polyetherketone, for example of polyetherether ketone (PEEK) or polyetherketoneketone (PEKK).

According to various exemplary embodiments, in c), the difference between the first pixel characteristic and the second pixel characteristic is determined.

The determination of the relationship can comprise, for example, establishing the ratio and/or determining the distance between the first pixel characteristic and the second pixel characteristic.

For example, at least two pixel characteristics can be determined which occur with a relatively high frequency, the distance between the at least two pixel characteristics being determined.

In c), for example, the contrast can be determined.

The relationship from c) can be associated with an established chemical resistance of the workpiece and/or with an established dimensional accuracy of the workpiece.

According to various exemplary embodiments, the first and second areas form a pattern, the pattern being detected, compared with predetermined patterns and associated with one of the predetermined patterns. Material characteristics with value ranges for the relationship of the first areas to the second areas can be respectively associated with the predetermined patterns. A material characteristic can be determined using the relationship determined in c) and the associated pattern.

The predetermined patterns correspond for example to different fiber inlays, for example to rovings, which are used as a starting material in the production of the component.

According to various exemplary embodiments, the image data recording and a) to c) are integrated into a component production, it being possible for the relationship determined in c) to be delivered to the component production as feedback.

According to various aspects, material characteristics of an aircraft component are determined by means of an optical analysis, said optical analysis comprising the evaluation of image data, for example of a photograph of the aircraft component. In case of a fiber-composite workpiece, for example, the crystallinity is determined using the detected image parameters, for example the grey value distribution or a color gradient. Since crystallinity can be an indication of the chemical resistance to aggressive fluids, this characteristic can easily be tested and thus ensured according to the present disclosure. This test can be carried out within a very short time, so that for example with a production cycle time of two minutes, the test can be adapted to the production cycle. In this respect, the test can also be carried out automatically and can thus form a simple quality control.

Furthermore, it can also be established according to the present teachings whether the mold has differing temperatures, i.e. temperatures which differ too much for the production of the component. For this purpose, for example, a plurality of recordings of different areas can be made which are then supplied to the determination procedure according to the present teachings. If the individual areas differ too greatly from one another in the established material characteristics, i.e. for example in their crystallinity, this implies that the mold has differing temperatures.

If, for example, a two-part mold is used with two mold halves, a respective temperature sensor is usually used, for example one temperature sensor in the upper half and one in the lower half, which corresponds, for example, to an outside of the component and to an inside of the component (based on the operating site). If the outside and the inside look the same, i.e. if they have the same crystallinity, it is possible to dispense with one of the sensors.

When divided molds are used, in which at least one of the mold halves includes a plurality of segments which are screwed together, it is possible to dispense with sensors in each of the segments, and instead to provide one sensor in the mold half. It is then possible to dispense with additional temperature sensors and with the reading or evaluation thereof. For example, it is then possible for one temperature sensor to be provided.

For an appraisal or estimation or assessment of the material characteristics, it is possible to provide a reference for each material, for example by a master comparison or a reference stored in a database.

These and other aspects are explained and illustrated with reference to the various exemplary embodiments described hereafter.

A person skilled in the art can gather other characteristics and advantages of the disclosure from the following description of exemplary embodiments that refers to the attached drawings, wherein the described exemplary embodiments should not be interpreted in a restrictive sense.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit application and uses. Furthermore, there is no intention to be bound by any theory presented in the preceding background or summary or the following detailed description.

Figure 1:
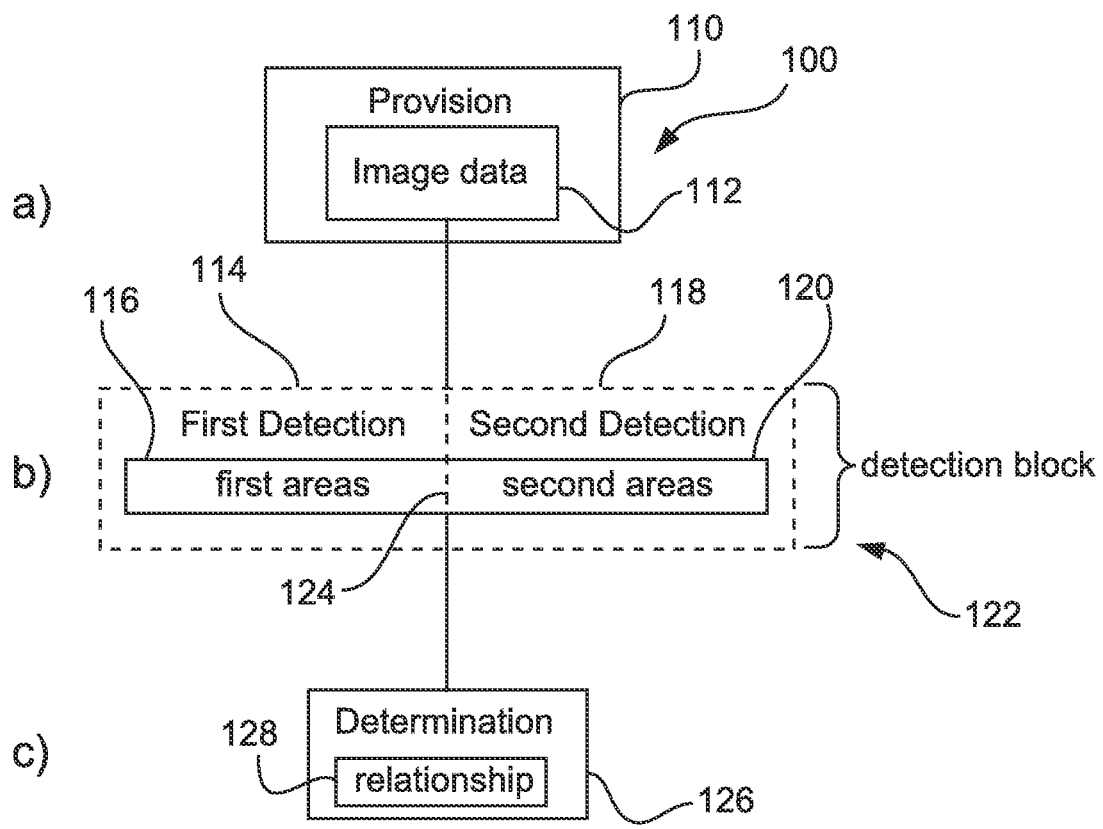
FIG. 1 shows a method for non-destructive determination of material characteristics of an aircraft component according to one of various examples.

FIG. 1 shows a method 100 for non-destructive determination of material characteristics of an aircraft component, which method comprises the following: in a provision block 110, image data 112 are provided of a layer, detectable from outside using electromagnetic radiation, of a workpiece to be examined. In a first detection sub-block 114, first areas 116 having a first pixel characteristic are detected using the image data. In a second detection sub-block 118, second areas 120 having a second pixel characteristic are detected using the image data. The two detection sub-blocks 114, 118 thus form a detection block 122 which is shown symbolically in FIG. 1 by a dashed frame enclosing the two detection sub-blocks 114, 118. A dashed line 124 between reference numeral 116 for the first areas and reference numeral 120 for the second areas indicates that the two areas are detected separately from one another, namely in the detection sub-blocks mentioned. The first pixel characteristic is associated with a fiber inlay of a fiber composite layer, and the second pixel characteristic is associated with an at least part-crystalline thermoplastic polymer of the fiber composite layer, which thermoplastic polymer is in a crystalline state. In a determination block 126, a relationship 128 of the first areas to the second areas is determined.

In addition to the first and second areas, further areas, for example intermediate areas, can also be detected and displayed.

The aircraft component to be examined is, for example, a component including a fiber composite material or a component, which is at least partly constructed from fiber composite material.

The terms "pixel characteristic", "brightness", "color" etc. have already been defined above and thus reference will be made here to the definitions provided above.

The provision block 110 is also identified as a), the detection block 114 is also identified as b) and the determination block 126 is also identified as c).

Figure 2:
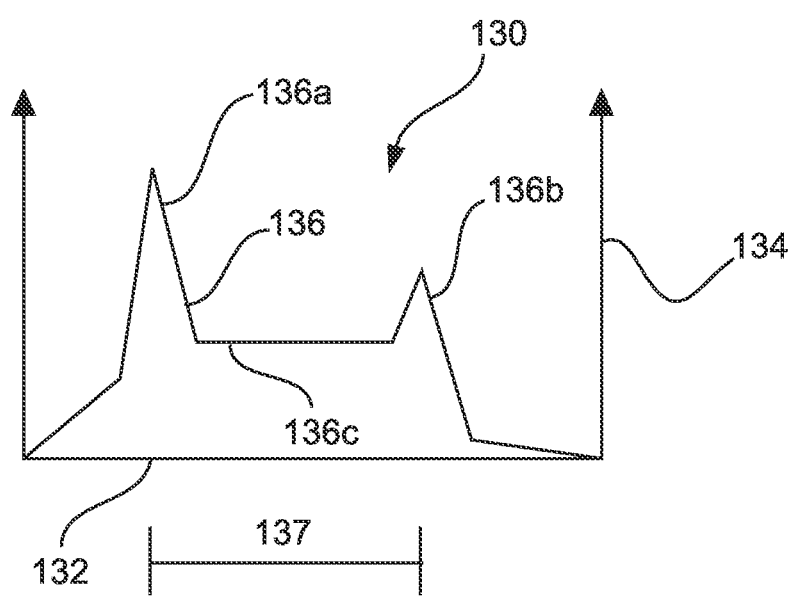
FIG. 2 shows a pixel characteristic course according to one of various examples.

According to various embodiments, for the determination of the relationship, a pixel characteristic course 130 is determined for the image data and is shown schematically in FIG. 2. In the pixel characteristic course 130, a spectrum of pixel characteristics is plotted on a horizontal axis 132. Plotted on a vertical axis 134 is a value for the respective pixel characteristic, i.e. a value of the respective pixel characteristic in relation to the distribution of the respective pixel characteristics in the detected image data. By joining the values for adjacent pixel characteristics, a curve or graph 136 is produced which represents the course of the pixel characteristics.

According to another exemplary embodiment of the method, although shown in connection with FIG. 2, but which can of course be combined as a separate variant with the other various embodiments, in other words, the method shown in FIG. 2 is also provided without the following procedure, in c) a difference 137 between the first pixel characteristic and the second pixel characteristic is determined, for example as a difference or distance value between the two distinctly higher areas 136a and 136b.

For example, the contrast can be determined in c) (not shown in further detail).

The pixel characteristic course also indicates, in addition to the values for the first and second areas, intermediate values or transition values of, for example, a joining segment 136c of the curve. If the workpiece showed the first and second areas, the curve would include the first peak and the second peak, and between these peaks it would run at the value "0". For example, a chessboard with black and white fields would have a first peak at the left-hand edge of the table and a second peak at the right-hand edge of the table.

Figure 3A:
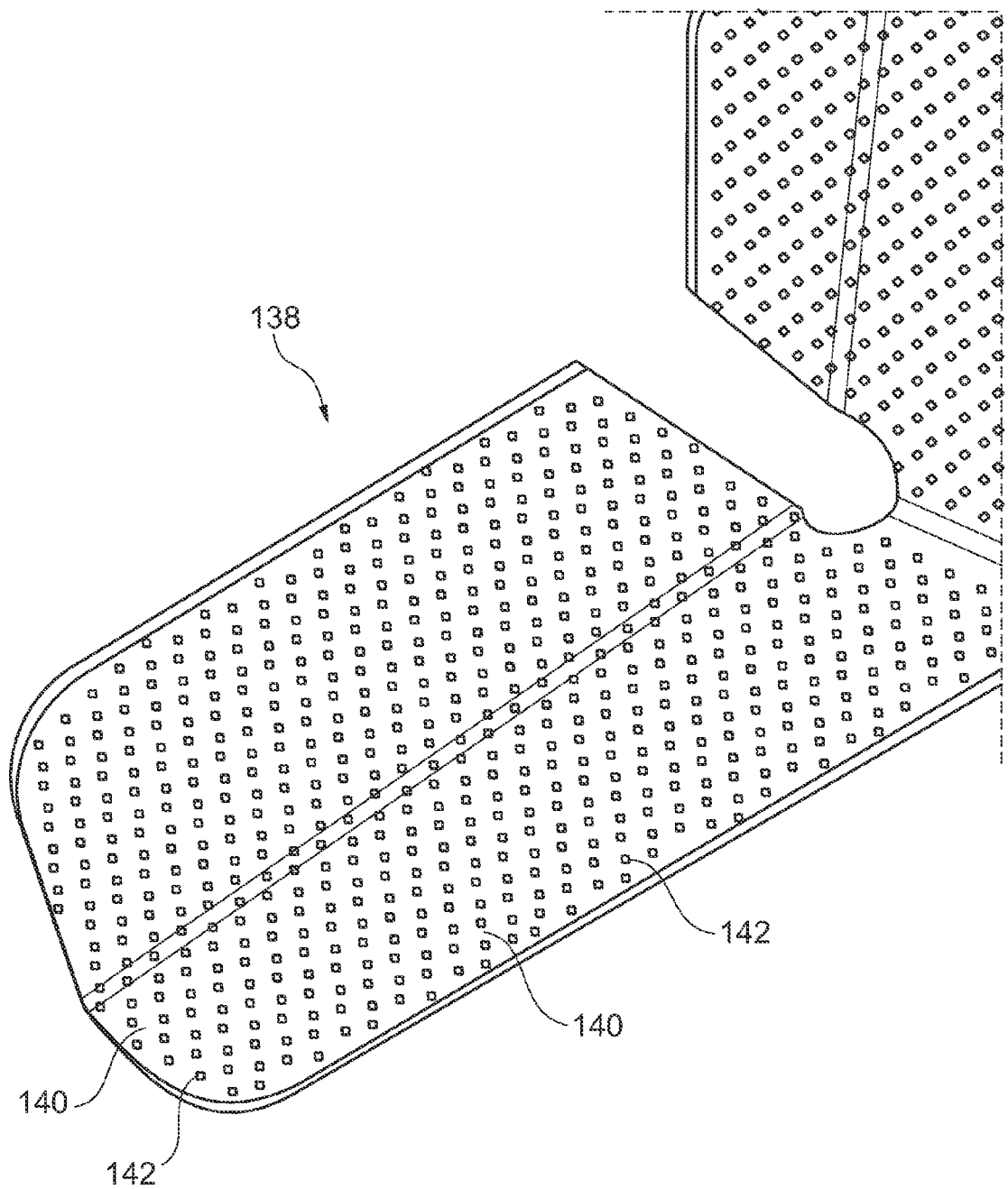
FIG. 3a is a graphic illustration of an example of an aircraft component to be examined.
Figure 3B:
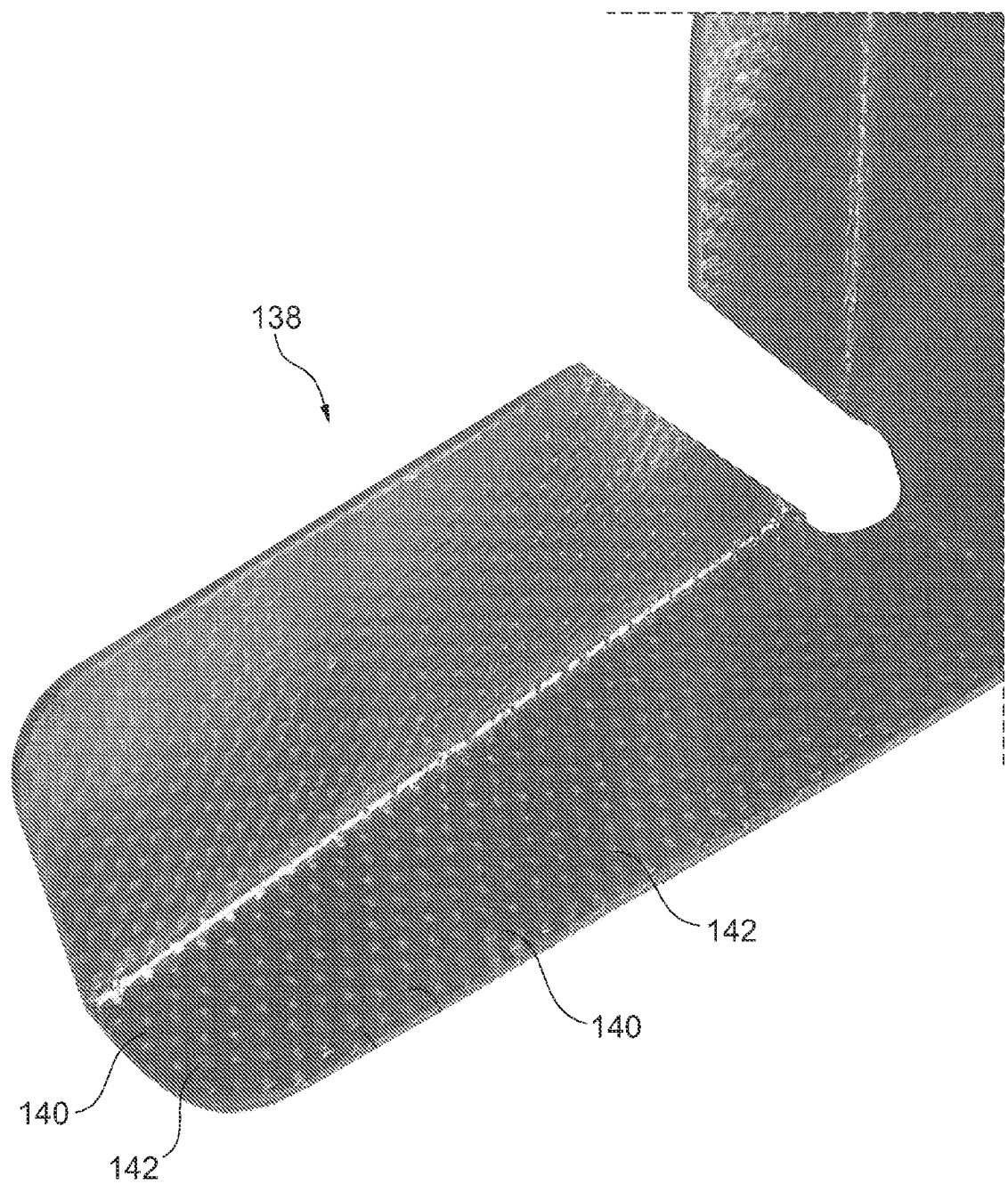
FIG. 3b shows a corresponding photographic image.

In the following, one of various exemplary embodiments will be described in more detail initially on the basis of a workpiece 138 shown in FIG. 3. FIG. 3a is the graphic illustration and FIG. 3b shows the photographic image. The workpiece 138 is a portion of a structure-connecting segment used for connecting the fuselage outer skin to the formers. The illustrated structure-connecting segment is also known as a clip. The illustrated clip is a composite component comprising thermoplastic material, for example of a carbon fiber-reinforced plastics material. However, it is pointed out here that according to various embodiments which are not shown, the material combinations mentioned above are provided instead of the carbon fiber-reinforced plastics material variant according to FIG. 3.

Due to the use of matrix material combined with a woven fabric, during production a visible layer, for example, is formed with first areas 140 and second areas 142 which are arranged in a more or less regular manner. The first areas are shown to be darker and indicate a fiber inlay of a fiber composite layer, which in this region forms the surface or the visible face. In between, the second areas are shown to be lighter, which indicates a matrix material including a part-crystalline thermoplastic polymer, which, in these regions, covers the fiber inlays located underneath. Since the part-crystalline thermoplastic material is visually different in the crystalline state from the fiber inlay, it is possible to detect the two different areas.

Since the areas of the matrix material in a crystalline state differ visually from the areas of the fiber inlay, it is possible to make a statement on the material characteristic, for example on the crystallinity, by means of the image.

Figure 3C:
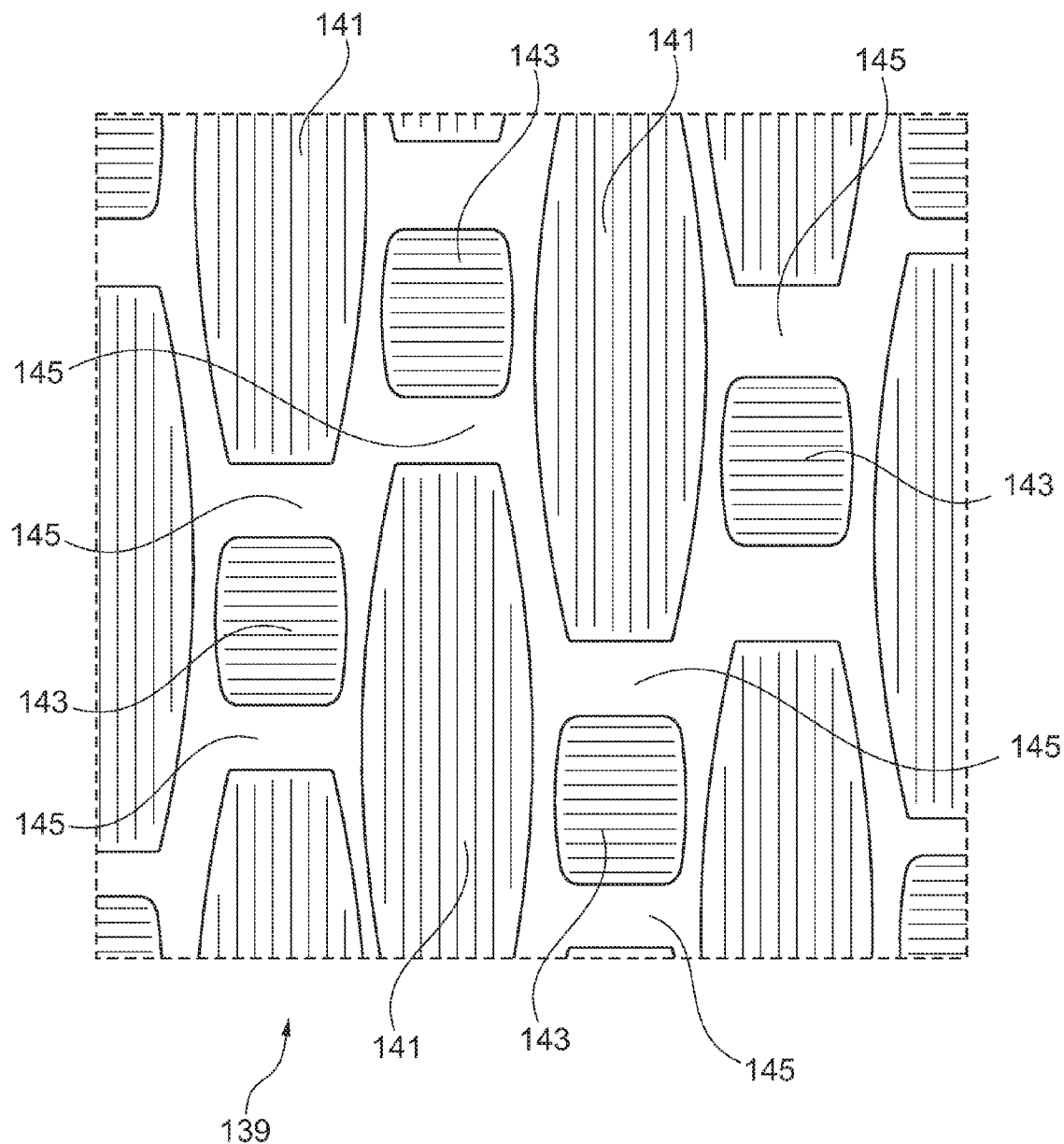
FIG. 3c is a graphic illustration of a unit cell as image data according to one of various examples and FIG. 3d shows a corresponding photographic image.
Figure 3D:
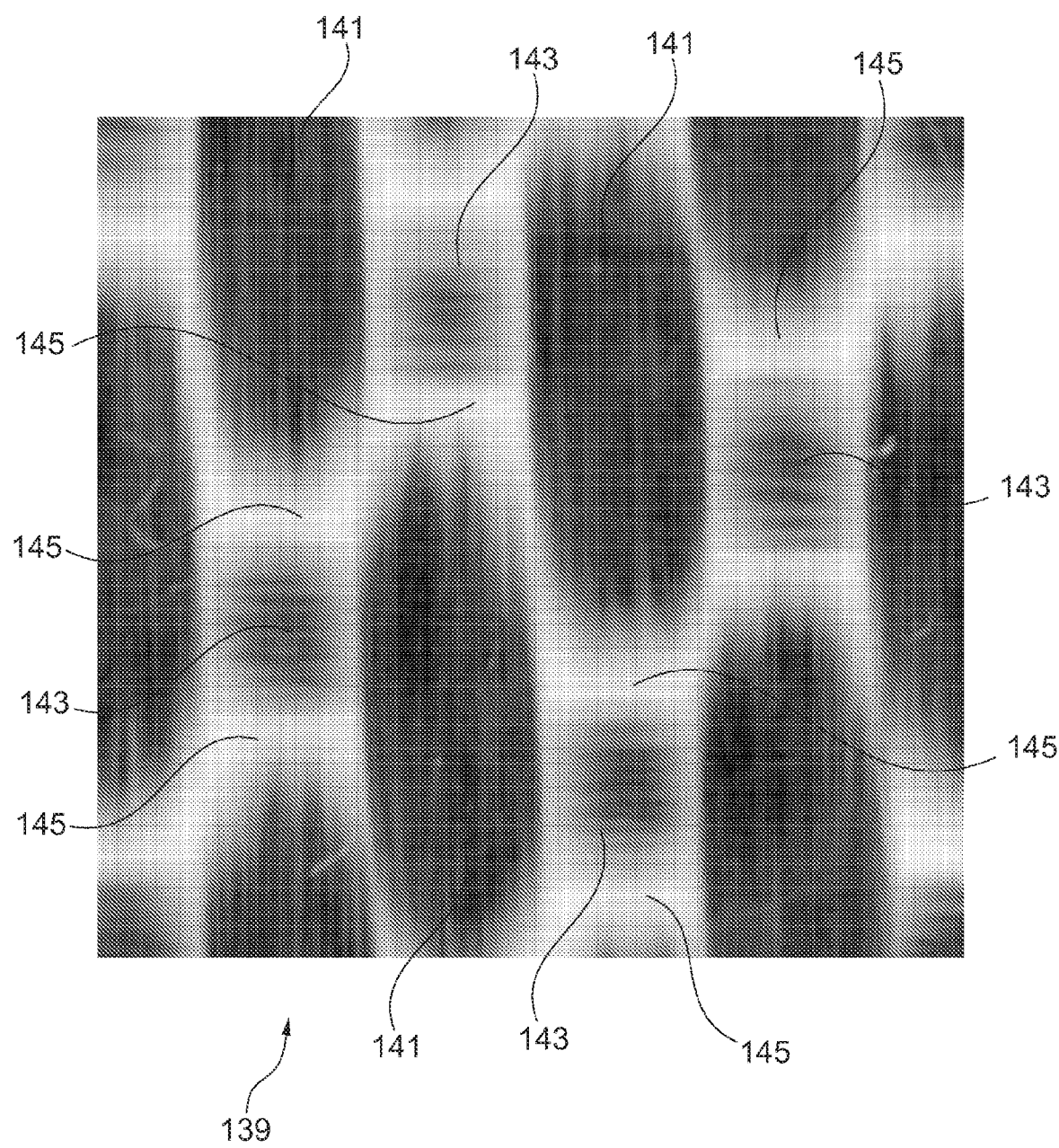

FIG. 3c shows a unit cell 139, which, in an image detail, has a fixed number of recurring image patterns or image structures. For example, it is possible to see areas of vertically running fiber bundles 141 and areas of fiber bundles 143 running transversely thereto, i.e. horizontally. Areas with matrix material 145 can be seen in between the bundles 141 and 143. The areas of the fiber bundles 141, 143 comprise substantially the first areas with first pixel characteristics, and the areas of the matrix material 145 comprise substantially the second areas with second pixel characteristics. In between, it is possible to see transition areas between the light second areas and the dark first areas.

Figure 4:
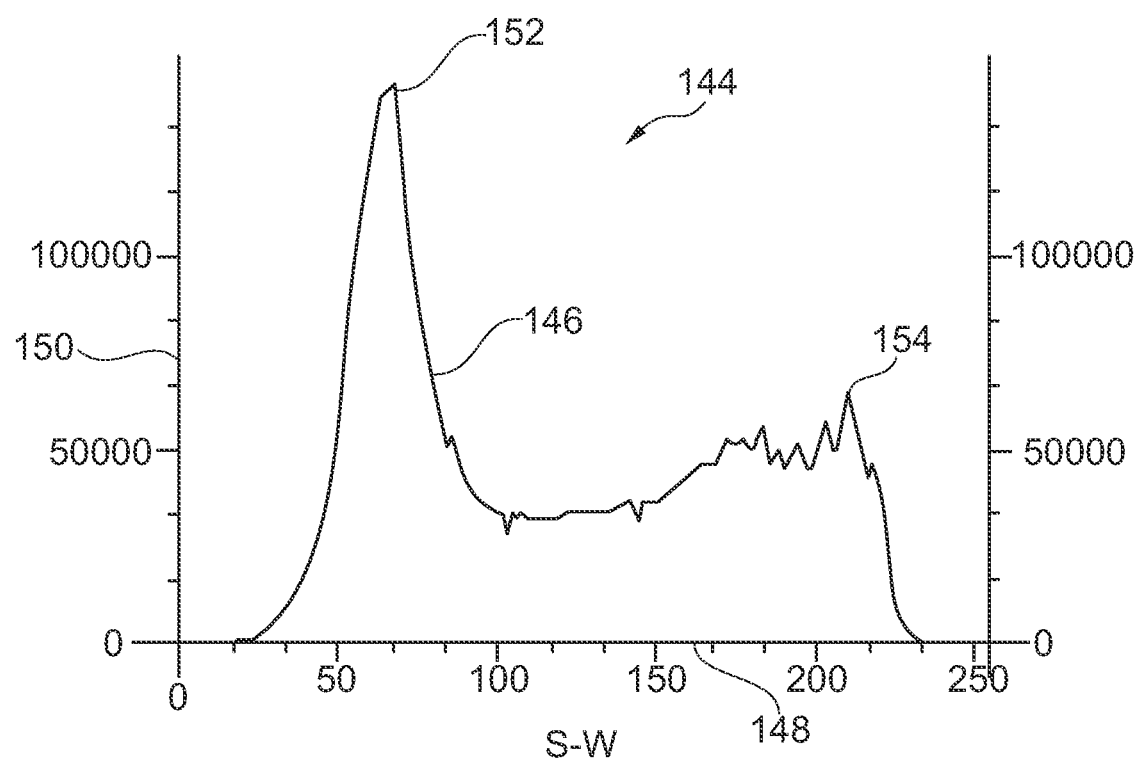
FIG. 4 shows one of various examples of a histogram.

For example, a detail of a visible surface of the component 138 can be provided as image data, so that it is possible to produce from this image detail a histogram 144, for example, which is shown in a first example in FIG. 4.

The histogram 144 represents in a curve 146 the distribution of individual pixel characteristics, for example for a grey value range of 0 to 255, which is plotted on a horizontal line 148. In this respect, the value 0 positioned on the left signifies a very dark grey value, namely black, and the value 255 provided on the right at the other end signifies a very light grey value, namely the color white.

The histogram 144 shows for the respective grey values on the grey value scale 148 the frequency which is to be encountered in the image data and is plotted on a vertical axis 150 with upwardly increasing values.

As can be seen from the illustration in FIG. 4, the curve 146 has a first higher area 152 with a culminating point or maximum value in the region of approximately 60.

Furthermore, a second prominent area 154 can be identified approximately in the region of 210.

The first area 152, projecting upwards as it were, indicates the frequency of the darker grey values and the second upwardly projecting area 154 indicates the frequency of the very light grey values.

Using the histogram 144, it can already be stated that in addition to the visible dark fiber areas, there is also a sufficient amount of light surface portions, which indicates a sufficient proportion of crystalline matrix material.

According to one example, it is also possible to provide a more approximate or more precise division of values, for example eight grey stage values, which produces a more approximate or more precise curve of the pixel characteristics.

If the first and second pixel characteristics are located closer together, i.e. if the two pixel characteristics do not differ very much from one another visually, the curve can also be considered in one portion. On the horizontal, the graph does not then show a spectrum from 0 to 255, but rather a portion of the value range.

Figure 5:
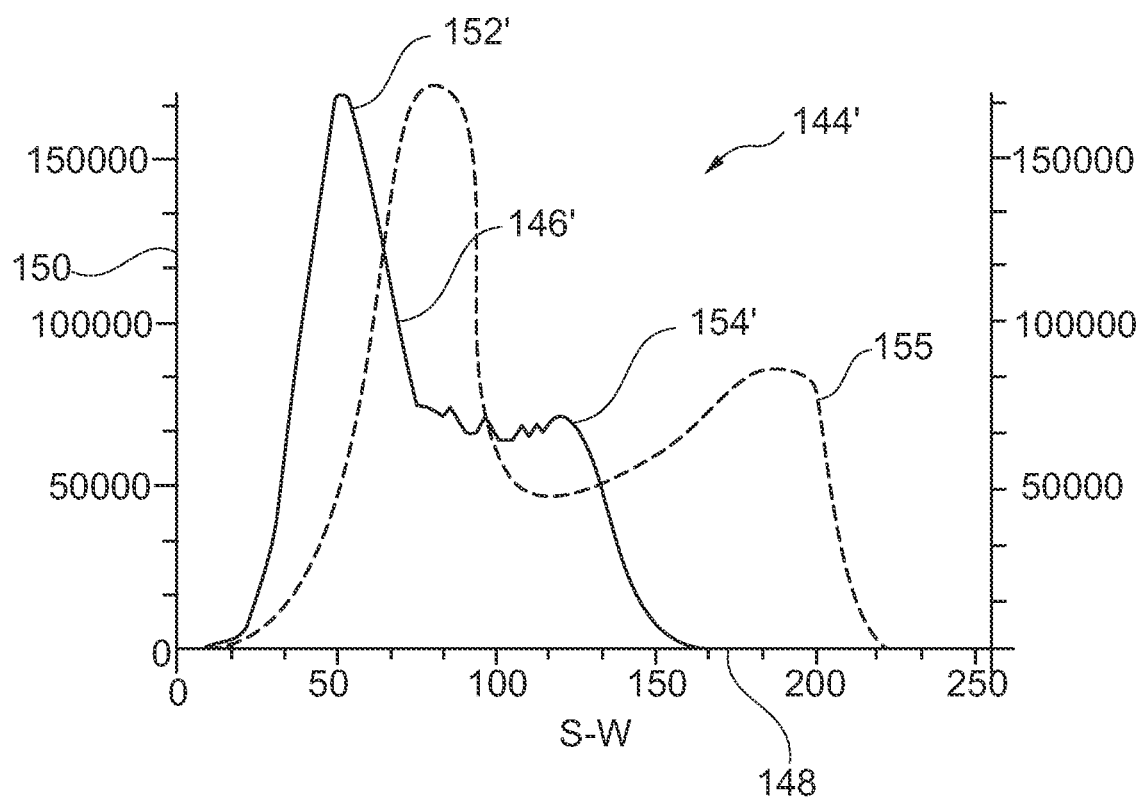
FIG. 5 shows another example of a histogram according to various embodiments.

Compared to FIG. 4, FIG. 5 shows a second histogram 144' in which a somewhat altered curve 146' is plotted.

In FIG. 5, a further variant is also suggested, in which, in addition to the illustrated histogram, an idealized target histogram is shown superimposed, which is indicated in FIG. 5 by a dashed line 155. This, so-called target histogram facilitates estimation or assessment of the determined histogram curve 154', because it can immediately be seen that the illustrated curve 154' differs significantly from the target histogram curve 155.

The target curve can indicate a minimum value; if the actual curve lies over the target curve, the component has the required characteristics or satisfies these characteristics. If the characteristics are to be within a range, the target curve can also be shown as a minimum curve and a maximum curve. If the actual curve is then located between the minimum curve and the maximum curve, the component is correct in respect of the measured characteristics.

A target curve allows simple detection and assessment of the examined characteristics.

The determined curve can also be automatically compared with the target curve, which will then merely show whether or not the component is in order. For example, the determined curve can be recorded onto the target curve. In this respect, for example deformation vectors are determined to ascertain the deviation from the target curve. Depending on the sign or direction, the vectors indicate whether the determined curve lies above or below the minimum value. Thereafter, the result can be output as "met" or "not met" and the components can be sorted out accordingly. In this manner, an incorrect interpretation by a user can be avoided. Furthermore, the evaluation can be incorporated directly into the production and a sorting procedure can take place in an automatically controlled manner.

The curve 146' shows a first maximum area 152' which is displaced slightly further in the direction of value 50 and a second maximum area 154' which is located in the region of approximately 120.

As can be seen in FIG. 5, the second area 154' is substantially less clearly pronounced than is the case for the histogram 144 in FIG. 4.

The differing course in FIG. 5 and in particular the substantially less pronounced second area 154', which has also moved closer to the first area 152', indicates that the markedness of light areas, which indicate the crystallinity of the matrix material due to the milky effect, is substantially weaker. In other words, it can be inferred from histogram 144' compared to histogram 144 that the material sample, on which FIG. 5 is based, or the examined component was not able to crystallise as effectively in the region of the outer surfaces as is the case for the component on which FIG. 4 is based.

Figure 6:
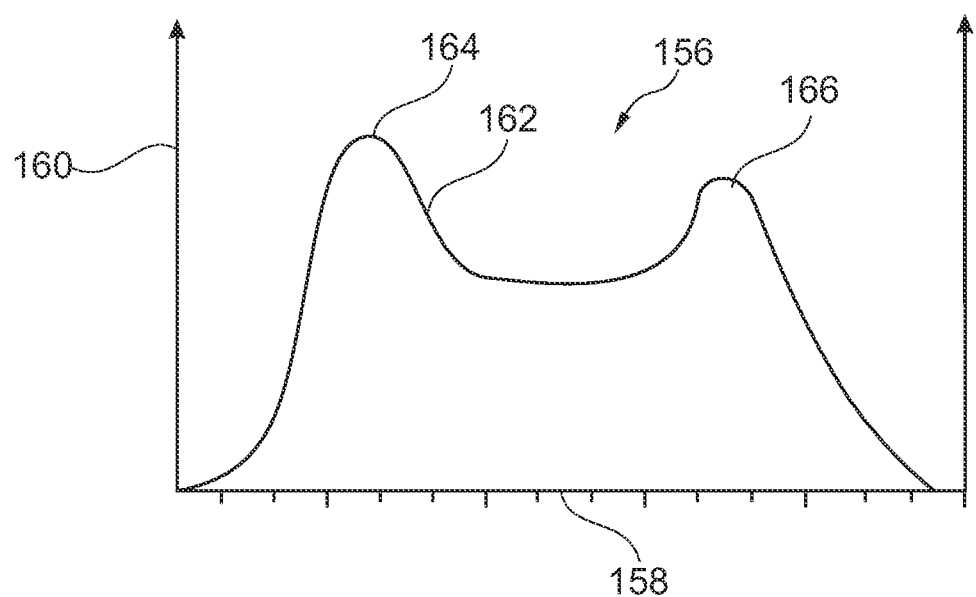
FIG. 6 shows an example of a colorcolor gradient according to various embodiments.

According to another one of various embodiments, the two areas, i.e. the first areas with a first pixel characteristic and the second areas with a second pixel characteristic, i.e. the areas which indicate the fiber inlay and the areas which indicate the at least part-crystalline thermoplastic polymer, are not distinguished by a strongly pronounced difference in brightness, for example by different grey values or grey value ranges, but by differently pronounced color values or color ranges. According to this embodiment, the pixel characteristic course is shown as a color gradient 146, as shown in FIG. 6. In the color gradient 156, the different values for the color range are plotted on a horizontal line 158 and the frequency of the color values found are plotted on a vertical line 160.

In FIG. 6, the color gradient 156 is shown as curve 162, which has a first higher area 164 and a second higher area 166, the first higher area 164 being positioned in the left-hand region and the second higher area 166 being positioned in the right-hand region.

If the fiber material used is material, which can be recognized by the color value range in the region of the first higher area 164, and the matrix material used has in the crystalline state a color value, which is significantly different therefrom and corresponds to the region of the second higher area 166, it can be inferred from the color gradient 156 that a sufficient quantity of crystalline areas have formed for example, it being possible to appropriately determine or define the term "sufficient". For example, this can be determined by a comparison with a reference pattern.

If the second higher area 166 were less strongly pronounced and also displaced in the direction of the first higher area 164, this would lead to the conclusion that less crystalline matrix material had formed.

Figure 7:
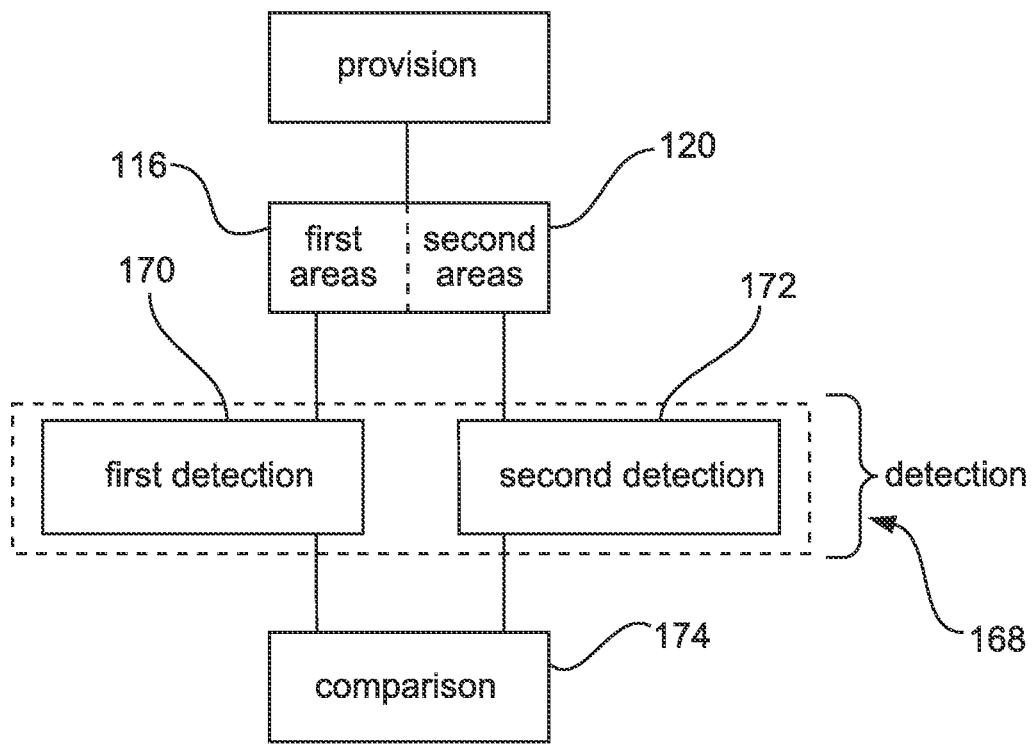
FIG. 7 to FIG. 14 show further various examples of methods according to various embodiments.

As an alternative and also in addition to the pixel characteristic course determination described above, it is also possible, as shown in FIG. 7, for the first areas 116 with the first pixel characteristic and for the second areas 120 with the second pixel characteristic to be detected in a detection block 168, indicated by a dashed frame in FIG. 7, which comprises a first detection sub-block 170 and a second detection sub-block 172. The detected first and second areas can then be compared with one another in a comparison block 174, for example by determining the totalled surface area measurements in each case. From the resulting relationship it is then possible to derive the corresponding information concerning the crystallinity.

Figure 8:
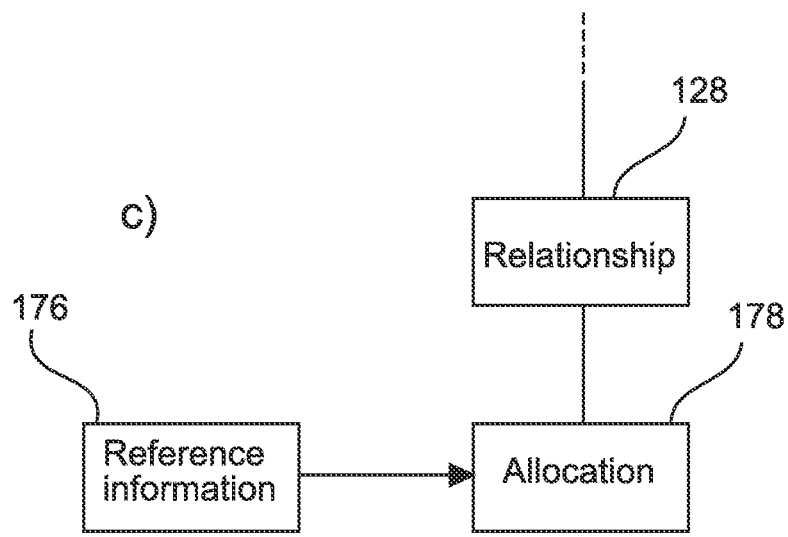

According to another of various examples of the method, as shown in FIG. 8, the relationship 128 from c) is allocated reference information 176 in an allocation block 178.

For example, a target curve or a target histogram can be displayed having the determined histogram or determined curve superimposed thereon.

Figure 9:
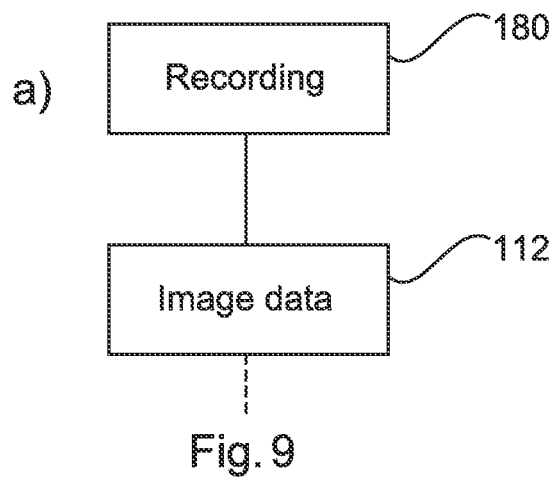

As shown in FIG. 9, another of various embodiments provides that for a), the image data 112 of the workpiece to be examined are recorded using electromagnetic radiation in a recording block 180, which precedes a).

For example, the image data are generated by light, the optical differentiation into first and second areas taking place in visible light or in invisible light, for example in infrared light or UV light.

According to one of various embodiments, the workpiece to be examined is guided along a recording device, for example a scanner or a camera, and the image data are provided by the recording device.

For example, image data can be recorded from different sides of the workpiece and made available, and a) to c) are carried out in parallel for the different sides.

Figure 10:
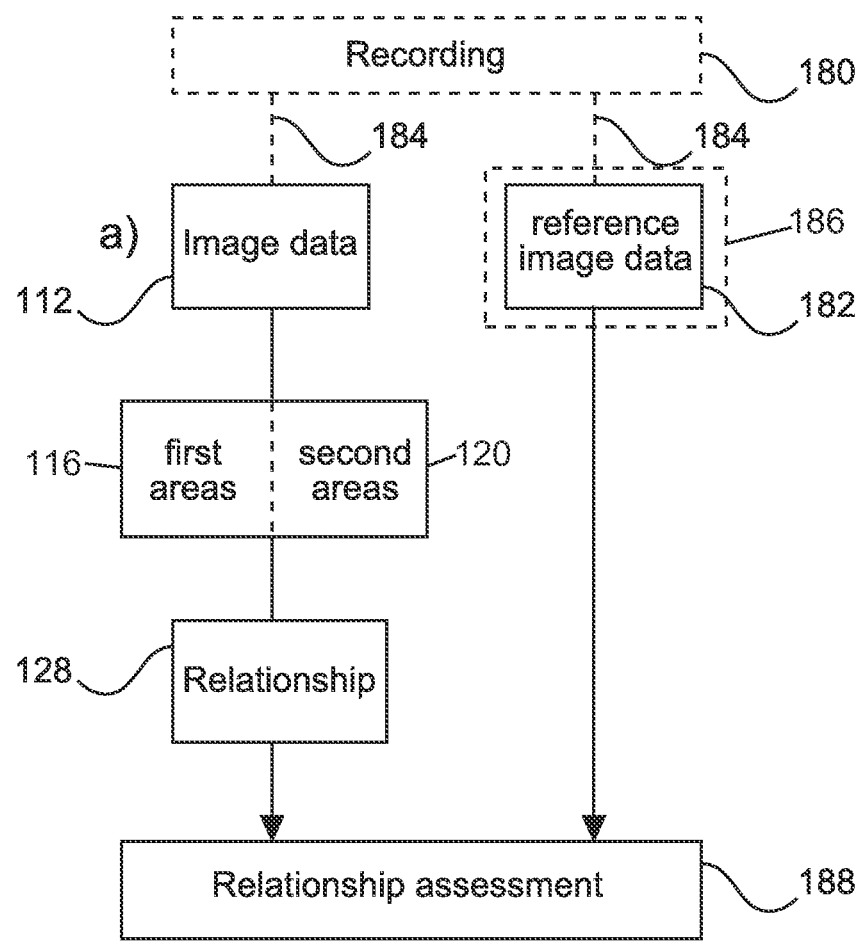

FIG. 10 shows another exemplary embodiment of a method, in which in a), reference image data 182 having first and second reference pixel characteristics are provided, which have been generated together with the image data, which is indicated by a frame 180 indicated at the top and by the dashed connection lines 184.

In this respect, a reference relationship 186 is stored. It is also shown in FIG. 10 that the relationship of the first areas to the second areas is assessed 188 using the reference relationship.

As already mentioned above, for example, a reference item can be detected together with the workpiece to thus form a criterion for the pixel characteristic, for example the brightnesses or the brightness values or colors or color values. For example, a chessboard pattern can also be recorded, which has established first pixel characteristics and established second pixel characteristics, or corresponding pattern areas. As a result, it is possible to achieve significant analyses even by means of different recording devices, which necessarily produce different image qualities.

In this respect, a chessboard pattern can have two different values, for example two different grey values or two different color values which correspond to the first and second pixel characteristics in their ideal form or which represent the intended values, for example a darker grey and a lighter grey or also black and white.

Figure 11:
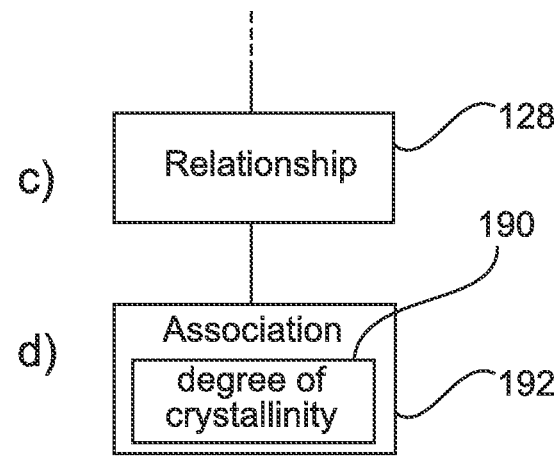

FIG. 11 shows another exemplary embodiment of a method, in which a d) is provided, in which the relationship 128 from c) is associated with an established degree of crystallinity 190 of the workpiece in an association block 192.

Figure 12:
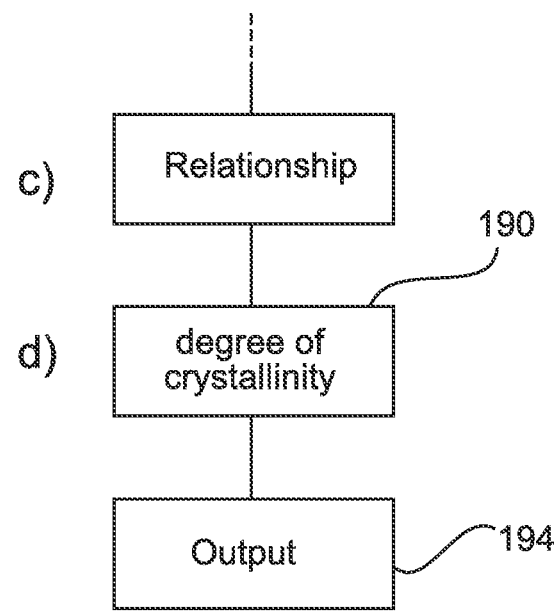

For example, the degree of crystallinity or the crystallinity value can be output, for example indicated, in an output block 194, as shown in FIG. 12.

Figure 13:
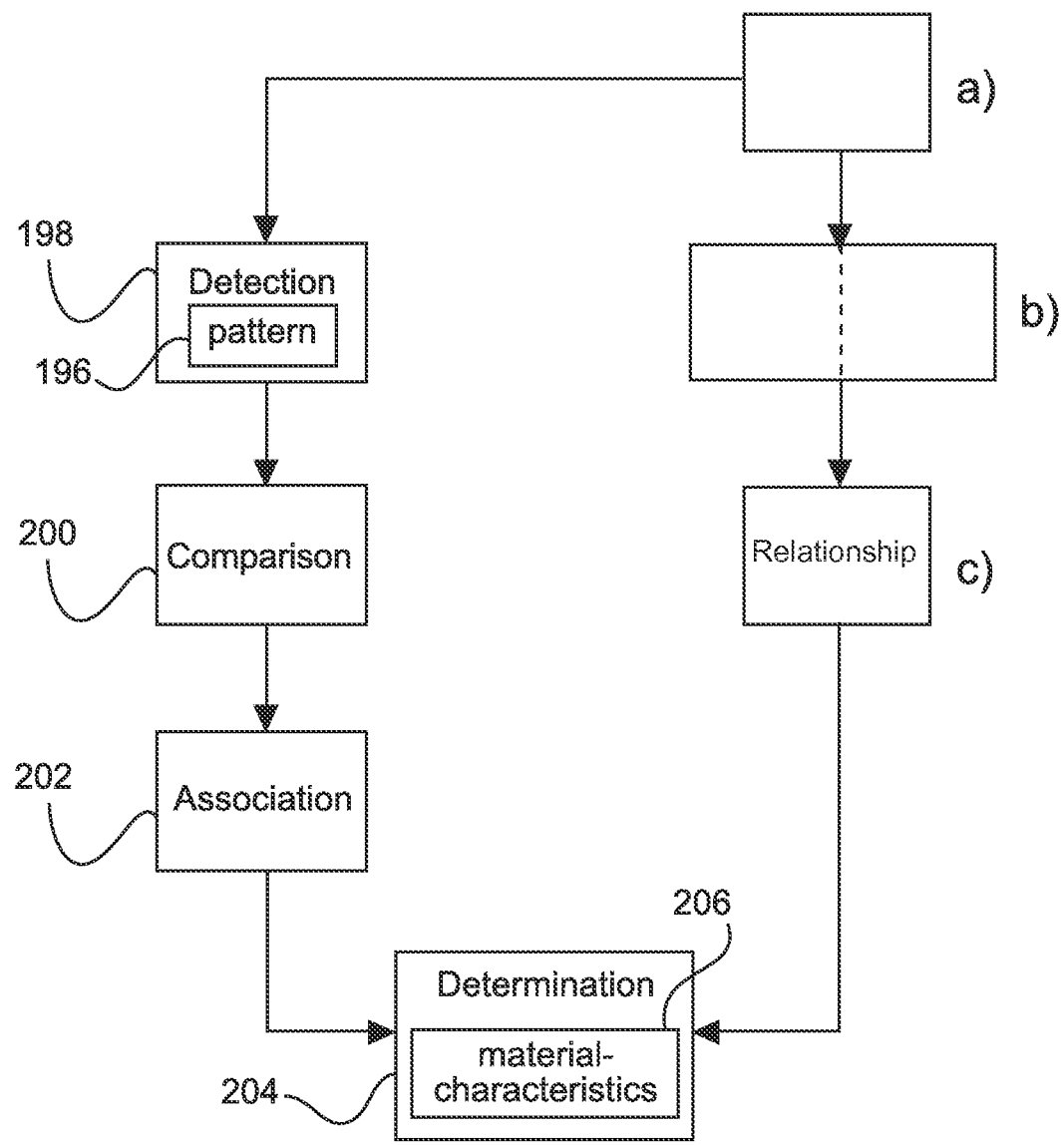

According to one of various embodiments shown in FIG. 13, the first and second areas 116, 120 form a pattern 196, this pattern being detected in a detection block 198, compared with predetermined patterns in a comparison block 200 and associated with one of the predetermined patterns in an association block 202. In this respect, material characteristics with value ranges for the relationship of the first areas to the second areas are respectively associated with the predetermined patterns.

A material characteristic 206 can then be determined in a determination block 204 using the relationship, determined in c), of the associated pattern.

For example, the predetermined patterns can correspond to different fiber inlays, so that different workpieces or components, which are constructed with different fiber inlays, rovings for example, pass through the ascertainment method without requiring a specific input of the respective type or type of fabric used.

Figure 14:
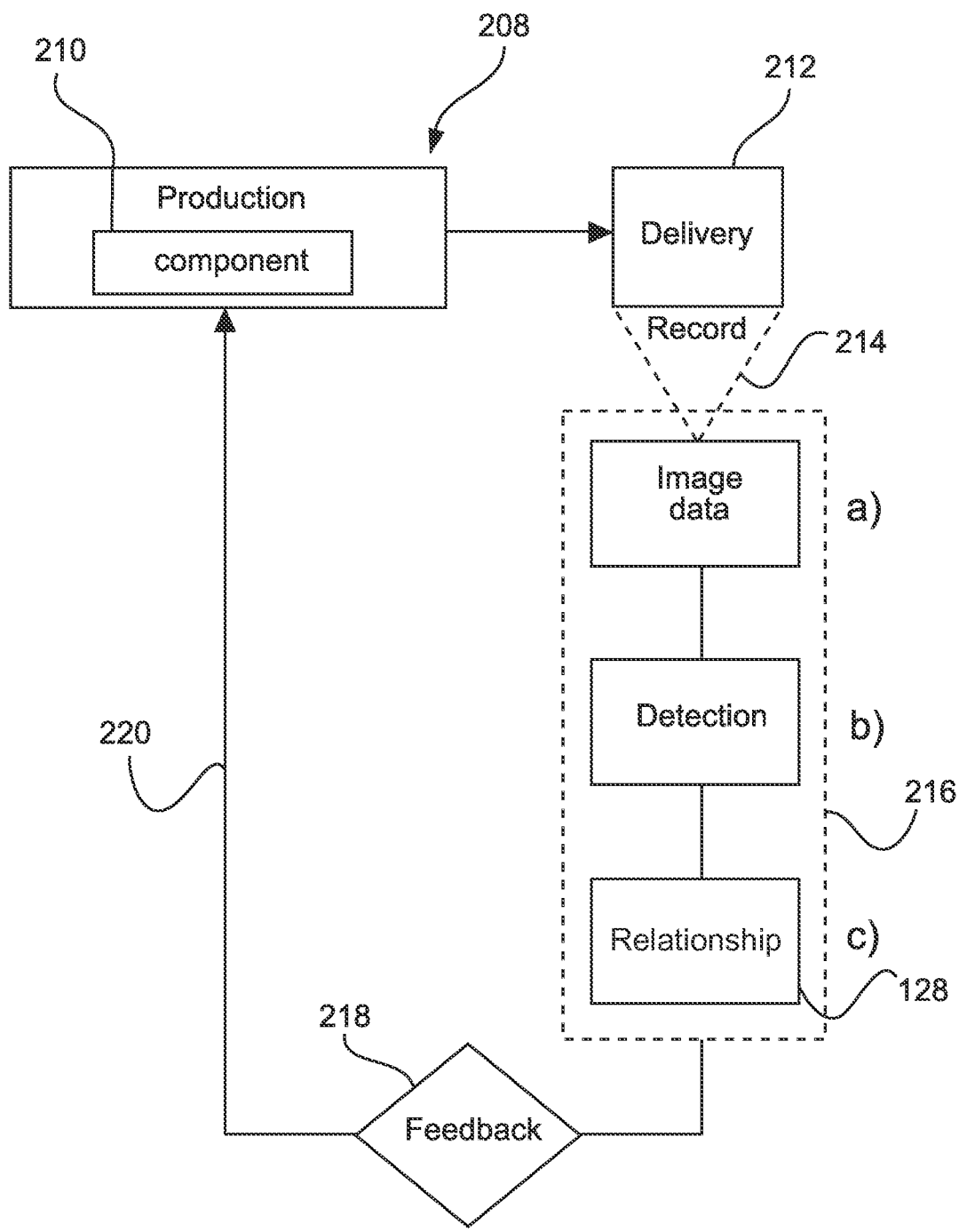

According to another exemplary embodiment illustrated in FIG. 14, the image data recording and a) to c) are integrated into a component production 208. In this respect, the actual component production is indicated by an oblong box 210 and the delivery of the component is indicated by a second smaller box 212 removed therefrom. As soon as the component is finished, the image data can be recorded, indicated by a pair of dashed lines 214 and the method according to the present teachings, which have been described in detail for determining material characteristics, can be carried out, which is indicated symbolically by a dashed box 216, although it is explicitly pointed out that the various embodiments and variants described above can of course also be used in connection with the component production of FIG. 14, and the variant of the present disclosure, illustrated in FIG. 14, is not restricted to a) to c) schematically indicated therein. The relationship 128 processed in c) or in one of the additionally provided routines can be delivered to the component production as feedback 218, which is indicated by a feedback arrow 220.

Figure 15:
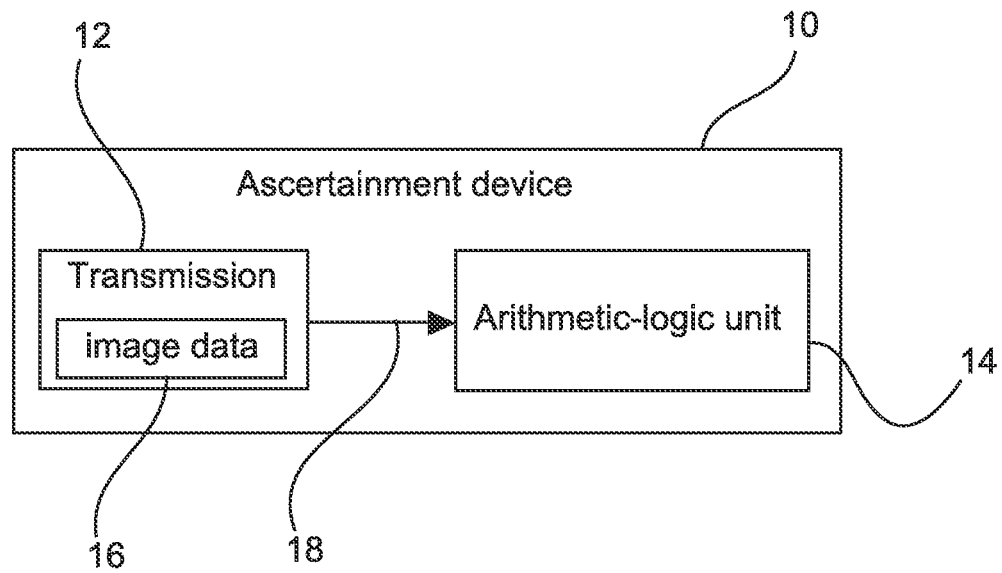
FIG. 15 shows an ascertainment device for the non-destructive determination of material characteristics of an aircraft component according to various embodiments.
Figure 16:
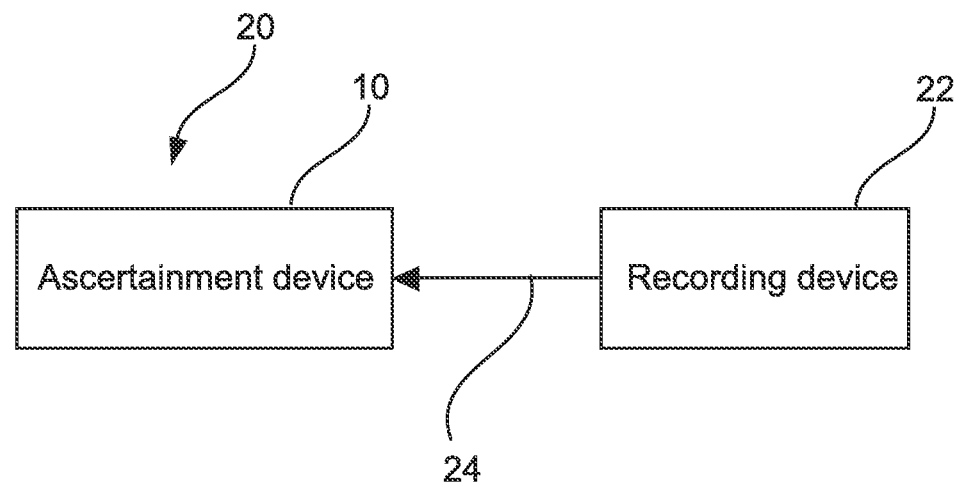
FIG. 16 shows a system for the non-destructive determination of material characteristics of an aircraft component according to various embodiments.

According to another exemplary embodiment, an ascertainment device 10 is also provided, which is shown in FIG. 15. The ascertainment device for the non-destructive determination of material characteristics of an aircraft component comprises a data transmission means 12 and an arithmetic-logic unit 14. The data transmission means 12 is configured to provide image data 16 of a layer, which can be optically detected from outside, of a workpiece to be examined, which is indicated by arrow 18. The arithmetic-logic unit 14 is configured to detect first areas having a first pixel characteristic and second areas having a second pixel characteristic using the image data, the first pixel characteristic being associated with a fiber inlay of a fiber composite layer and the second pixel characteristic being associated with an at least part-crystalline thermoplastics polymer of the fiber composite layer, which thermoplastics polymer is in a crystalline state.

The arithmetic-logic unit 14 is configured to determine the relationship of the first areas to the second areas.

Furthermore, a system 20 for the non-destructive determination of material characteristics of an aircraft component is provided, which comprises a recording device 22 for generating image data and an ascertainment device 10 according to the exemplary embodiment described with reference to FIG. 15. The recording device 22 is configured to record image data of a layer, which can be optically detected from outside, of a workpiece to be examined. The recording device 22 transmits the image data via the data transmission means 16 to the arithmetic-logic unit 14, the transmission to the ascertainment device 10 being indicated by arrow 24.

Figure 17A:
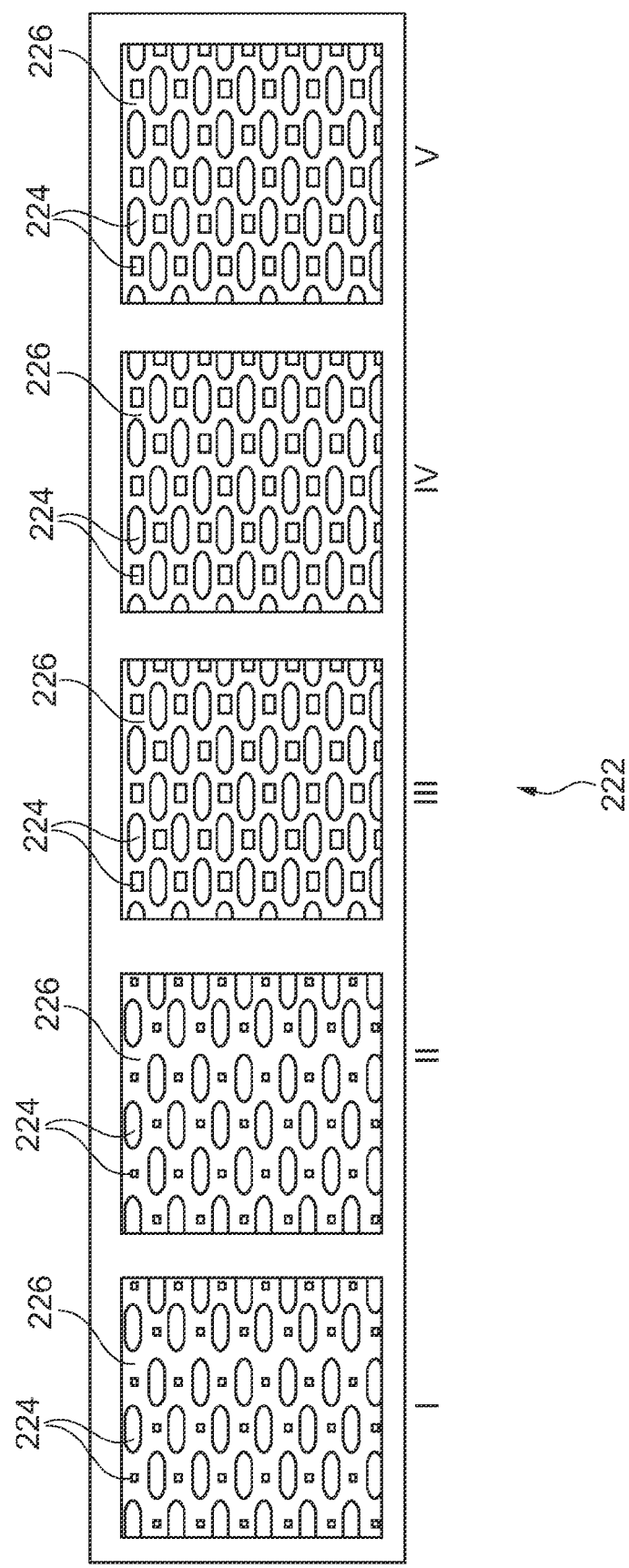
FIG. 17 shows another exemplary embodiment of the non-destructive determination according to the present teachings of material characteristics of an aircraft component, FIG. 17a showing a graphic illustration and FIG. 17b showing a corresponding photographic image.
Figure 17B:
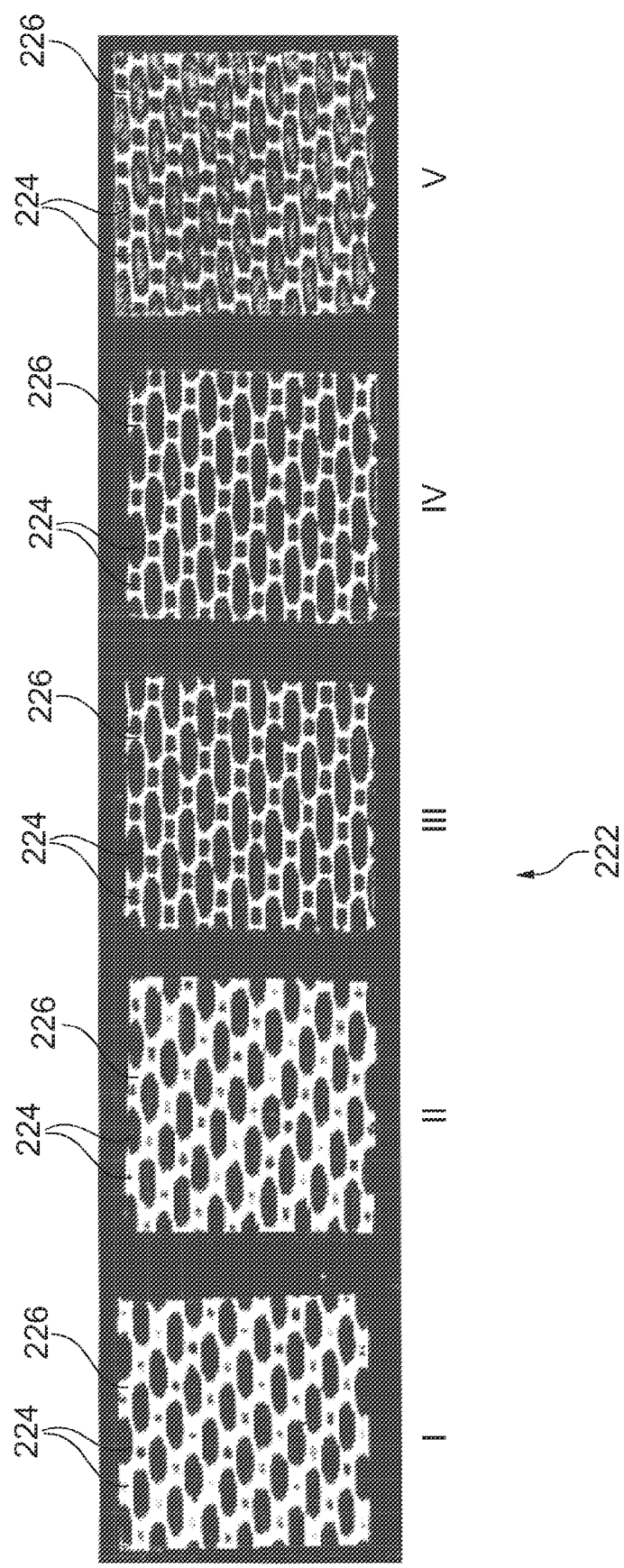

FIG. 17 shows five different image details 222, which illustrate different image data of a layer that can be detected from outside using electromagnetic radiation, for example light, of a workpiece to be examined and, for the sake of simplicity, have been numbered from I to IV in FIG. 17. FIG. 17a shows the graphic illustration and FIG. 17b shows the photographic image.

The image data have in each case dark areas 224 and light areas 226. As can be seen from a comparison of the five items of image data, the light and dark areas 224, 226 are arranged in the same pattern, which leads to the conclusion that the workpieces have each been produced with the same or with a similar fiber inlay. In the left-hand field, i.e. variant I, the light areas are substantially more clearly pronounced than is the case in variants III, IV or V.

A further difference lies in the transition between the darker areas and the lighter areas which is shown to be substantially more abrupt in variant I, while in variant II, grey values have formed in the transition region. This also applies to variant V, in which some of the light areas 226 are no longer joined together continuously.

Due to the detection according to the present disclosure of the first and second areas, i.e. the areas associated with the fiber inlay and the areas associated with the crystalline portion of the at least part-crystalline thermoplastic polymer, it is possible to gain information about the material characteristics of the respective components.

In variant I, the ratio or relationship existing between the dark areas and the light areas is such that the light areas occupy a greater proportion than is the case in variants II to V. The greater proportion of lighter areas indicates a greater formation of crystalline regions in the part-crystalline thermoplastic polymer, so that merely by evaluating the image, it is possible to state that variant I has a higher crystallinity value compared to variants II to V, which are shown with a decreasing crystallinity value. In other words, of the five illustrated components, the left-hand component, i.e. variant I, has a better chemical resistance to aggressive fluids.

As already indicated, the image evaluation also provides information about the dimensional accuracy of the component, which is particularly significant for those components which have an angular construction. In the case of at least part-crystalline thermoplastic polymers, after the component has been removed from the mold, different backwards and forwards adjustments are entailed, subject to the respectively formed crystallinity. The cause of this is, inter alia, that the amorphous and the part-crystalline molecular structures have different densities. The backwards and forwards adjustments can have different results, depending on the relationship between the amorphous and the part-crystalline structures. For example, to achieve an exact angle of about 90 degrees, it is often necessary to configure the mold with a slightly exaggerated angle of, for example, about 90+2 degrees, so that when the component is removed from the mold, an adjustment of about 90 degrees is produced. However, this forwards adjustment is carried out differently depending on the formation of the crystalline structure, so that for example in the case of a slightly crystalline matrix material, a relatively small forwards adjustment is produced, so that the component does not have an angle of exactly 90 degrees, but instead has an angle which possibly differs impermissibly therefrom.

According to one of various examples, it is therefore possible to provide information about the accuracy of the angles to be formed based merely on the evaluation of the image data, so that it may not be necessary to re-measure the angle. Of course, this applies to those components, for which an exact adjustment of the angle is produced due to a sufficient crystallinity, as well as to those components, for which an intolerable angle is produced, because a fixed limiting value for the crystallinity has not been met.

It is also mentioned with respect to FIG. 17 that the illustrated samples, i.e. components I to V, have crystallinity values of 29.3% for variant I, 28.1% for variant II, 23.4% for variant III, 22.5% for variant IV and 18.7% for variant V.

In a further exemplary embodiment, a computer program or computer program element is provided, which is adapted to implement the method on a suitable system according to any one of the previous embodiments.

For this, the computer program element can be stored on a computer unit, which can also be part of one of various embodiments of the present disclosure. The computer unit or arithmetic-logic unit can be configured to implement the method described above or to initiate implementation. Furthermore, the computer program element can be configured to operate the components of the device described above. The computer program can be loaded into the main memory of a data storage unit. The arithmetic-logic unit can be equipped to implement the method of according to the present teachings.

This exemplary embodiment relates to both a computer program, which uses the present teachings from the start, and to a computer program element, which, by means of an update, converts an existing program into a program that uses the present teachings.

Furthermore, the computer program element can be capable of providing all the necessary routines to carry out the procedure of one of the various embodiments of the method which have been described above.

According to another exemplary embodiment, a computer-readable medium such as a CD-ROM is provided, the computer-readable medium having stored a computer program element which has been described in the previous paragraphs.

The computer program can be stored or distributed on a suitable medium so that an optical storage medium or a read-only memory, supplied together or as part of another hardware, are also distributed in another manner, for example via the Internet or other wired or wireless telecommunications systems.

However, the computer program can also be provided via a network such as the Internet and can be downloaded from a network into the main memory of a data processor. According to another exemplary embodiment, a medium is provided to make a computer program element available for downloading, the computer program element being configured to implement a method according to any one of the various embodiments which are described above.

The various embodiments described above can be combined in different ways. In particular, aspects of the method can also be used for various embodiments of the devices and for uses of the devices and vice versa.

In addition, it should be noted that "comprising "does not exclude any other elements or blocks and "a" does not exclude a plurality. Furthermore, features or blocks which have been described with reference to one of the above embodiments and aspects can also be used combined with other features or blocks of other embodiments and aspects described above. In addition, while at least one exemplary embodiment has been presented in the foregoing summary and detailed description, it should be appreciated that a vast number of variations exist. It should also be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing an exemplary embodiment, it being understood that various changes may be made in the function and arrangement of elements described in an exemplary embodiment without departing from the scope as set forth in the appended claims and their legal equivalents.

What is claimed:

1. An ascertainment device for non-destructive determination of material characteristics of an aircraft component, comprising:
    a data transmission device that provides image data of a layer, which is optically detected from an outside of a workpiece to be examined; and
    an arithmetic-logic unit; that detects first areas having a first pixel characteristic and second areas having a second pixel characteristic using the image data, the first pixel characteristic being associated with a fiber inlay of a fiber composite layer, and the second pixel characteristic being associated with an at least part-crystalline thermoplastic polymer of the fiber composite layer, the thermoplastic polymer having a crystalline form or an amorphous form; and
    the arithmetic-logic unit determines a relationship of the first areas to the second areas,
    wherein the arithmetic-logic unit visually distinguishes the crystalline form from the amorphous form and visually distinguishes the fiber inlay from the crystalline form of the thermoplastic polymer.

2. A system for non-destructive determination of material characteristics of an aircraft component, comprising:
    a recording device to generate image data and record image data of a layer, which is optically detected from outside of a workpiece to be examined; and
    an arithmetic-logic unit that detects first areas in the image data having a first pixel characteristic and second areas in the image data having a second pixel characteristic, the first pixel characteristic being associated with a fiber inlay of a fiber composite layer, and the second pixel characteristic being associated with an at least part-crystalline thermoplastic polymer of the fiber composite layer, and the arithmetic-logic unit determines a relationship of the first areas to the second areas,
    wherein the thermoplastic polymer has a crystalline form or an amorphous form;
    wherein the arithmetic-logic unit visually distinguishes the crystalline form from the amorphous form and visually distinguishes the fiber inlay from the crystalline form of the thermoplastic polymer; and
    wherein the recording device transmits the image data to the arithmetic-logic unit via a data transmission means.

3. A method for the non-destructive determination of material characteristics of an aircraft component, comprising:
    a) providing of image data of a layer, which is detected from outside using electromagnetic radiation of a workpiece to be examined;
    b) detecting first areas having a first pixel characteristic using the image data, and detecting second areas having a second pixel characteristic using the image data, the first pixel characteristic being associated with a fiber inlay of a fiber composite layer, and the second pixel characteristic being associated with an at least part-crystalline thermoplastic polymer of the fiber composite layer, which thermoplastic polymer is in a crystalline state; and
    c) determining a relationship of the first areas to the second areas,
    wherein the thermoplastic polymer has a crystalline form or an amorphous form and the method further comprises:
    visually distinguishing the crystalline form from the amorphous form; and
    visually distinguishing the fiber inlay from the crystalline form of the thermoplastic polymer.

4. The method according to claim 3, wherein for the determination of the relationship, a pixel characteristic course for the image data is determined.

5. The method according to claim 3, wherein determining the relationship of the first areas to the second areas is associated with an item of reference information.

6. The method according to claim 3, wherein providing of the image data of the workpiece to be examined further comprises:
    recording the image data using electromagnetic radiation.

7. The method according to claim 3, wherein providing image data of a layer further comprises:
   providing reference image data having first and second reference pixel characteristics, which have been generated together with the image data; and
   providing a reference relationship being stored,
   wherein the relationship of the first areas to the second areas is assessed using the reference relationship.

8. The method according to claim 3, wherein the relationship of the first areas to the second areas is associated with an established degree of crystallinity of the workpiece.

9. The method according to claim 3, wherein the first pixel characteristic is associated with a fiber inlay, which comprises carbon fibers.

10. The method according to claim 3, wherein determining the relationship of the first areas to the second areas further comprises:
    determining the difference between the first pixel characteristic and the second pixel characteristic.

11. The method according to claim 3, wherein the first and second areas form a pattern and the method further comprises:
    detecting the pattern;
    comparing the detected pattern with predetermined patterns, the predetermined patterns including material characteristics having value ranges for the relationship of the first areas to the second areas;
    associating the detected pattern with one of the predetermined patterns; and
    determining a material characteristic using the relationship of the first areas to the second areas and the associated pattern.

12. The method according to claim 3, wherein the image data recording and a) to c) are integrated into a component production; and the relationship, determined in c), is delivered to the component production as feedback.

13. A non-transitory computer readable medium embodying a computer program product, said program product comprising:
    a non-destructive determination of material characteristics of an aircraft component program, the non-destructive determination of material characteristics of an aircraft component program configured to:
    provide image data of a layer, which is detected from outside of a workpiece to be examined using electromagnetic radiation;
    detect first areas having a first pixel characteristic using the image data, and detect second areas having a second pixel characteristic using the image data, the first pixel characteristic associated with a fiber inlay of a fiber composite layer, and the second pixel characteristic associated with an at least part-crystalline thermoplastic polymer of the fiber composite layer, which thermoplastic polymer is in a crystalline state; and
    determine a relationship of the first areas to the second areas;
    wherein the thermoplastic polymer has a crystalline form or an amorphous form, and the program is further configured to:
    visually distinguish the crystalline form from the amorphous form; and
    visually distinguish the fiber inlay from the crystalline form of the thermoplastic polymer.

14. The program product according to claim 13, wherein for the determination of the relationship, a pixel characteristic course for the image data is determined.

15. The program product according to claim 13, wherein the program is further configured to record the image data using electromagnetic radiation.

16. The program product according to claim 13, wherein the program is further configured to:
    provide reference image data having first and second reference pixel characteristics, which have been generated together with the image data; and
    provide a reference relationship being stored,
    wherein the relationship of the first areas to the second areas is assessed using the reference relationship.

17. The program product according to claim 13, wherein the relationship of the first areas to the second areas is associated with an established degree of crystallinity of the workpiece.

18. The program product according to claim 13, wherein the first pixel characteristic is associated with a fiber inlay, which comprises carbon fibers.

* * * * *